(12) United States Patent
Bobrowski

(10) Patent No.: US 6,797,286 B2
(45) Date of Patent: Sep. 28, 2004

(54) METHODS AND PREPARATIONS OF EXTRACTS OF UNCARIA SPECIES WITH REDUCED ALKALOID CONTENT

(75) Inventor: Paul J. Bobrowski, Scottsdale, AZ (US)

(73) Assignee: Rainforest Nutritionals, Inc., Phoenix, AZ (US)

(*) Notice: Subject to any disclaimer, the term of this patent is extended or adjusted under 35 U.S.C. 154(b) by 0 days.

(21) Appl. No.: 10/674,986

(22) Filed: Sep. 30, 2003

(65) Prior Publication Data

US 2004/0068130 A1 Apr. 8, 2004

Related U.S. Application Data

(60) Provisional application No. 60/416,730, filed on Oct. 5, 2002.

(51) Int. Cl.[7] .............................................. A61K 35/78
(52) U.S. Cl. ...................................................... 424/725
(58) Field of Search .......................................... 424/725

(56) References Cited

U.S. PATENT DOCUMENTS

| | | | |
|---|---|---|---|
| 4,844,901 | A | 7/1989 | Keplinger et al. |
| 4,940,725 | A | 7/1990 | Keplinger et al. |
| 5,302,611 | A | 4/1994 | Keplinger et al. |
| 5,723,625 | A | 3/1998 | Keplinger et al. |
| 6,039,949 | A | 3/2000 | Pero |
| 6,238,675 | B1 | 5/2001 | Pero |
| 6,264,994 | B1 * | 7/2001 | Castillo et al. ............. 424/725 |
| 6,361,805 | B2 | 3/2002 | Pero |

OTHER PUBLICATIONS

Medical Botany, Lewis et al., published 1977 by John Wiley & Sons (NY), pp 277–279 and 509.*
Mark JS Miller et al., Dietary antioxidants protect gut epithelial cells from oxidant–induced apoptosis, BMC Comp and Alternative Med Dec. 2001, I:II, U.S.
M. Sandoval et al., Anti–inflammatory and antioxidant activities of cat's claw (*Uncaria tomentosa* and *Uncaria guianensis*) are indept . . . , Phytomedicine 9:325–337, 2002, U.S.
J Piscoya et al., Efficacy and safety of freeze–dried cat's claw in osteoarthritis of the knee: mechanisms . . . , Inflamm.res.50(2001) 442–448, U.S.
M Sandoval et al., Cat's Claw Inhibits TNalpha Prod. and Scavenges Free Radicals: Role in Cytoprotection, Free Radical Biology & Med, vol. 29 No. 1 pp 71–78,2000, U.S.
R Aquino et al, New quinovic acid glycosides from Uncaria Tomentosa, J Natural Prod, vol. 51, No. 2, pp 257–261, Mar.–Apr. 1998, U.S.
G Konwalinka, Capillary electrophoretic analysis of oxidole alkaloids from *Uncaria tomentosa*, J of Chromatography, 609 (1992) pp 375–380, U.S.
H Stuppner et al, HPLC Analysis of the Main Oxidole Alkaloids from *Uncaria tomentosa*, Chromatography, V 34, No 11/12, Dec. 1992, U.S.
G. Laus et al., Separation of Stereoisomeric oxidole alkaloids from *Uncaria tomentosa* by high performance liquid chromatography, J Chromatography, A, 662 (1994) U.S.
Y Sheng et al, Induction of Apoptosis and Inhibition of Proliferation of Human Tumor Cells Treated with Extracts of *Uncaria Tomentosa*, Anticancer Research 18:3363–3368 (1998).
M Sandoval–Chacon, Antiinflammatory actions of cat's claw: the role of NF–κB, Aliment Pharmacol Ther 1998;12;1279–1289 U.S.
K Keplinger et al, *Uncaria tomentosa* (Willd.) DC.–Ethnomedicinal use and new pharmacological, toxicological and botanical results, J Ethnopharmacology 64 (1999) 23–34 U.S.
Y Sheng et al, Enhanced DNA repair, immune function and reduced toxicity of C–MED–100, a novel aqueous extract from *Uncaria tomentosa*, J Ethnopharmacology 69 (2000) 115–126 US.
S Lamm, Persistant response to pneumococcal vaccine in individuals supplemented with a novel water soluable extract of *Uncaria tomentosa*, C–MED–100® Phytomedicine, vol. 8(4) pp. 267–274 U.S., no date provided.

* cited by examiner

Primary Examiner—Raymond J. Henley, III
(74) Attorney, Agent, or Firm—Ellis & Venable, P.C.

(57) ABSTRACT

The method herein describes a process for the preparation and extraction of components from plants of the family Rubiaceae indigenous to South America, also known as Cat's Claw or Uña de gato. Cat's claw is an ethnomedicine that contains a variety of constituents, some of which have opposing actions. Oxindole and pentacyclic alkaloids have been proposed to be constituents that stimulate immune function, whereas polar constituents act to suppress immune response. An extract that was devoid of the aforementioned alkaloids would avoid opposing actions that may negate effectiveness or limit therapeutic outcome.

14 Claims, 1 Drawing Sheet

US 6,797,286 B2

METHODS AND PREPARATIONS OF EXTRACTS OF UNCARIA SPECIES WITH REDUCED ALKALOID CONTENT

This application claims benefit of U.S. Provisional Application Ser. No. 60/416,730 filed on Oct. 5, 2002.

BACKGROUND OF THE INVENTION

1. Field of the Invention.

The present invention is relevant to the field of anti-inflammatories and anti-oxidants and the manufacture of anti-inflammatories and anti-oxidants.

2. Discussion of the Related Art.

The indigenous inhabitants of the Amazon forests refer to plants from the Uncaria species as Uña de Gato ("Cat's claw"). These inhabitants traditionally used the Uncaria plant(s) in a raw unprocessed botanical form as a treatment for a wide array of health disorders. More specifically, ethnomedical preparations of Uncaria plant(s) were and are today consumed as decoctions or teas made from the bark of Uncaria brewed in water. Numerous researchers propose that the Uncaria chemical constituents, and particularly the alkaloids oxindole and pentacyclic, are responsible for its immune enhancing action of the plant material.

Today, Cat's Claw is marketed and sold as an herbal medicine throughout the world. The primary form of these commercial preparations entails the manual manipulation of the bark, root or leaves to produce varying particulate powders. Said powders are then encapsulated for oral administration at a suggested dosage of 1–3 grams of crude material per day. It is not obvious nor has it been taught that these commercial preparations for Uncaria duplicate its historical efficacy. As of this writing, a review of the literature reveals that there has never been a single peer-reviewed scientific article demonstrating any human efficacy or health benefits derived from the oral consumption of the crude plant parts of Uncaria. Furthermore, since the solid matter from teas or decoctions is discarded (e.g. as a tea bag), it is unclear whether this solid matter would in fact cause stomach irritation, toxicity or limit the absorption of Uncaria's active ingredients.

Researchers have identified inherent immunostimulating as well as immunosuppressant actions caused by the diverse chemical constituents of the Uncaria species. Researchers have determined that Uncaria's immunostimulating actions are attributable to alkaloids, pentacyclic and oxindole, that are more lipophilic than the transcriptionally active immunosuppressant components. There is prior and established art for the extraction and concentration of these lipophilic and immunostimulating alkaloids by various methods primarily utilizing alcohol rather than water as the extracting agent.

Related art exists for the extraction, concentration and determination of Uncaria's lipophilic alkaloids extractions with higher alkaloid concentrations (U.S. Pat. Nos. 4844901, 4940725, 5302611, 5723625). The method uses aqueous ammonia pretreatment followed by supercritical extraction. The resultant material has been indicated for unspecific stimulation of the immune system as characterized by increased macrophage phagocytosis.

Related art also exists that teaches that a hot water extraction of the crude plant parts of Uncaria and the subsequent dialysis of the solubilized products yields a composition which has a high degree of the immune stimulatory activities (U.S. Pat. Nos. 6039949, 6238675, 6361805). These activities were confirmed through increased lymphocyte phagocytosis and cytokine production and more recently, increased vaccine response. However, while increased leukocyte phagocytosis and cytokine production are characteristics of the immune response, they contribute to tissue injury during states of inflammation. Thus, current therapeutic approaches in treating inflammatory disorders usually seek to lower cytokine levels and inhibit leukocyte activity.

SUMMARY OF THE INVENTION

Aspects of the invention are summarized below to aid in the understanding of embodiment(s) of the invention and the application. Yet, the invention is fully defined by the claims of the application.

In contrast to its immunostimulating alkaloids, preparations or decoctions of Uncaria plant material also exhibit an inherent immunosuppressive and anti-inflammatory result. This dichotomy between the immunostimulatory (pro-inflammatory) alkaloids and the immunosuppressive (anti-inflammatory) agents, concurrent yet opposing actions—stimulation and suppression—limit the true potential and benefits of either component. Thus, a method of distinguishing and removing from Uncaria decoctions the immunostimulatory alkaloids would result in an Uncaria extract with enhanced efficacy and therapeutic potential of the polar, immunosuppressive, TNF-alpha inhibiting agents. The present invention describes an extract and method for extracting or depleting from plants of the Uncaria species (Cat's Claw or Uño de gato) it's lipophilic, immunostimulating alkaloids whilst retaining and then further concentrating its polar, immunosuppressive agents. The process generally comprises an organic extraction(s) and drying of decocting crude Uncaria plant parts. The resulting Uncaria extract is substantially deplete of immunostimulatory actives and retains enhanced anti-inflammatory components and antioxidant capacities.

The Uncaria extract described herein demonstrates antioxidant activity and also an ability to inhibit the formation of inflammatory and immune mediators like tumor necrosis factor alpha (TNFalpha) by suppressing the activation of genes associated with inflammation and the immune response. This transcriptional inhibition likely results from suppression of nuclear factor kappa B (NF-kB) and functions to suppress an over active immune response that contributes to tissue injury during states of inflammation. It is counterintuitive that the enhancement and concentration of known immunostimulatory (i.e. pro-inflammatory) alkaloids would act as immunosuppressants and exert any anti-inflammatory activity.

This invention demonstrates that the Uncaria extract by the process disclosed herein is characterized by enhanced immunosuppressant and anti-inflammatory action and therefore requires an effective dose twenty times less (i.e. 2 mg/kg) than extracts or decoctions produced by other methods. Anti-inflammatory and transcriptionally acting immune modulating actions of the Uncaria extract preparations described herein have application in disorders characterized by NF-kB activation, oxidant burden, enhanced cytokine production and cell death. These disorders include, but are not limited to, arthritis (both osteoarthritis and rheumatoid), inflammatory bowel disease (IBD), gastritis, chronic inflammation of the eyes, skin, liver, muscles and kidney, fibromyalgia, atherosclerosis, and Alzheimer's disease.

DESCRIPTIONS OF EMBODIMENTS

Figure 1:
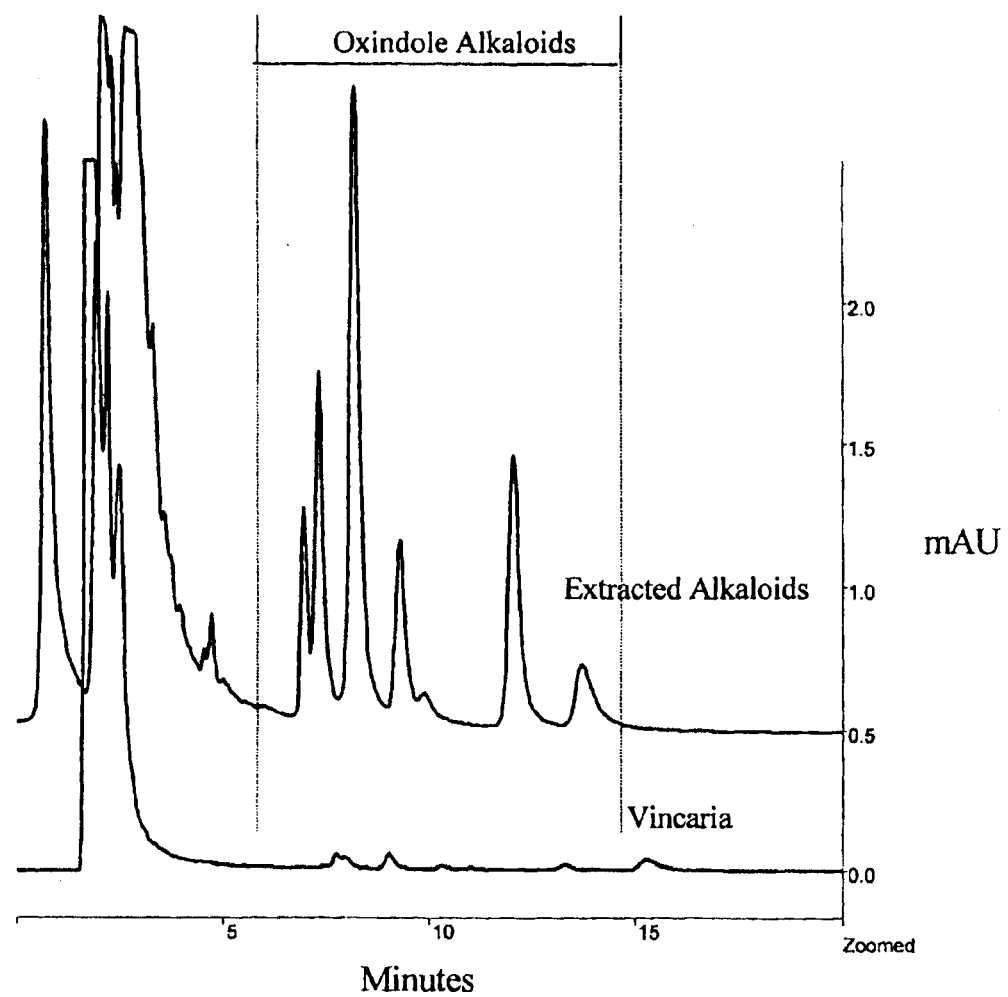
FIG. 1. A comparison of Uncaria parent and extract by high performance liquid chromatography (HPLC). As shown in the overlaid chromatograms, the Uncaria extract derived from the methods described herein (Vincaria™) is substantially deplete of the immunostimulating alkaloids found in the parent (Uncaria spp) whilst retaining and thus enhancing the efficacy and therapeutic potential of the polar, immunosuppressive and TNF-alpha inhibiting (antinflammatory) components.

The Uncaria extract(s) prepared by the processed disclosed herein result in a composition that is low in alkaloid content. The descriptions are exemplary methods for the purpose of resolving the extract. An ordinarily skilled practitioner could conceive of variations of the methods in light of the disclosure and the results to be achieved.

Extraction Process 1

An aqueous extract of the Uncaria species is achieved by a decoction method as previously described. A preferred decoction comprises a quantity of raw or dried botanical in hot water. More specifically, solid matter of the plant material such as roots, bark and or powders of genus Uncaria are mixed in such a ratio with water that when heated for a period of time at a temperature of approximately 90–100 degrees centigrade, with or without agitation, to yield a brown aqueous extract also known as a decoction or tea. The decoction or tea is then filtered of all solid matter for further processing according to one aspect of the invention. The filtrate is subsequently dried to remove all aqueous components. Acceptable drying methods include air-drying, evaporation, or vacuum drying or an equivalent.

An organic solvent Is subsequently added to the dried decoction or extract. A preferred organic solvent is chloroform/methanol (2:1) added in a volume-to-volume ratio of 1:1 to 1:20. Another suitable organic solvent is ethyl acetate. The dried decoction and organic solvent are mixed and subsequently separated. One preferred manner of separating the polar constituents and alkaloids of the dried decoction involves exposure of the dried decoction to organic solvent. One convenient means of exposure comprises placement of the dried concoction into a sack or bag, constructed of paper cotton or other equivalent materials, and immersion in organic solvent. Following exposure, the bag is subsequently removed from the organic solvent and dried to eliminate any residual organic solvent. Drying resolves the genus Uncaria extract comprised of polar constituents and largely deplete of the alkaloids captured by the organic solvent. Drying and may be accomplished by one or more drying processes including heating, air drying, freeze drying or vacuum drying. Depletion of alkaloids content is confirmed by high performance liquid chromatography (HPLC) as indicated in FIG. 1.

Extraction Process 2

An aqueous extract of the Uncaria species is achieved by a decoction method as previously described. To this extract in its liquid phase the organic solvent ethyl acetate, is added. Following agitation and settling the organic layer is separated from the aqueous and the organic layer discarded. The solutes remaining in the aqueous layer are the resolved by drying. Several drying processes can be used: heating, air-drying, freeze-drying, or vacuum drying. Depletion of alkaloids content is confirmed by high performance liquid chromatography (HPLC) as indicated in FIG. 1.

Extraction Process 3

This process employs the same decoction extraction method as described for Examples 1 and 2, but before the extraction of organic material is employed; the solute in the decoction is isolated by drying. To this dried powder the organic solvents are added (chloroform/methanol, 2:1: or ethyl acetate). This mixture is agitated for adequate mixing, followed by settling. The liquid organic solvent is removed and discarded, and the solutes are dried again as outlined by similar methods employed for drying in Example 1 or 2. Depletion of alkaloids content is confirmed by high performance liquid chromatography (HPLC) as indicated in FIG. 1.

Table 1: Antioxidant and anti-TNFalpha actions of cat's claw formulations. Note that in order to assess activity in micropulverized Uncaria, a hot water extraction was performed and this decoction used for evaluation. TNFapha production was assessed in cultured macrophages (RAW 264.7 cells) stimulated with bacterial endotoxin (LPS: 0.5 µg/mL). After one hour exposure to LPS, media was collected and TNFalpha levels measured by ELISA. DPPH scavenging was spectophometerically measured by a reduction in absorbance at 515 nm. Results are depicted as $IC_{50}$, which is the concentration that produces a 50% inhibition. A lower $IC_{50}$ value is indicative of greater potency. Note: For each assay, potency was significantly greater in alkaloid depleted freeze-dried formulation when compared to the other formations ($P<0.01$)

| Assay $IC_{50}$ | Freeze-dried Alkaloid Deplete Uncaria (Vincaria ™) | Freeze-dried Uncaria Alkaloid Intact | Micropulverized Uncaria Alkaloid Intact |
|---|---|---|---|
| DPPH | 12.6 µg/mL | 20.8 µg/mL | 150 µg/mL |
| Anti-TNFalpha | 9.5 ng/mL | 14.1 ng/mL | 28 ng/mL |

Antioxidant Activity

The extract processed according to the invention and produced from freeze-dried Uncaria plant matter a composition with enhanced antioxidant activity or ability to scavenge the stable free radical 2,2'-dipyridyl-2-pyridylhydrazone (DPPH) as compared to those preparations made from the manual manipulation of the bark, root or leaves to produce particulate powders. As demonstrated in Table 1, it has a lower 50% effective concentration (IC50) for scavenging DPPH radicals than compared powdered formulations.

Inhibition of TNFα Formation

The extract processed according to the invention and produced a composition with an enhanced ability to inhibit the formation of tumor necrosis factor alpha (TNFα) by macrophages stimulated by bacterial endotoxin [lipopolysaccharide (LPS)]. This activity is superior to the compared powdered formulations as well as freeze-dried preparations containing higher alkaloid content (Table 1). This supports the indication that the alkaloid constituents of the Uncaria species are not the components responsible for its immunosuppressive activity but rather suggest their role in the enhancement of the immune system.

Alkaloid Depletion

Uncaria derived alkaloids (both pentacyclic and oxindole) have been suggested as the constituents responsible for its immuno-enhancing activity. However, in the treatment of inflammatory disease, the enhancement of the immune response is counter-productive while the suppression of an overactive immune system is the more common and logical approach to therapy and a target for therapeutic innovations. Thus, for enhanced anti-inflammatory actions, it is necessary to deplete effective Uncaria formulations of these alkaloids.

The extraction method herein described entails the concentration of Uncaria's active components by decoction and then the depletion of the alkaloid content through chemical manipulation with organic solvents. More particularly, the Uncaria extract is significantly deplete of oxindole, pentacyclic and tetracyclic alkaloid when compared to the parent botanical. These alkaloids are more lipophilic than the active antioxidant and NF-κB suppressive components. Thus, treatment of a decoction of Uncaria plant material with an organic solvent to resolve the aqueous (i.e. non-organic components) significantly reduces the alkaloid content whilst retaining the polar anti-inflammatory compounds. As clearly shown in Table 1, specific alkaloids used as markers to quantify the resultant composition's alkaloid content demonstrate 35-fold depletion with an associated improvement in antioxidant and anti-TNFα action.

Laboratory results indicate that the oxindole alkaloid content of the Uncaria extract processed as described herein is less than 0.3 mg/g of dired decoction. Decoctions are generally 20% of the parent Uncaria plant material. Thus, the non-alkaloid components are 5 times concentrated, or approximately 0.06 mg/g of raw botanical. Normal or starting detected values of oxidole alkaloid content are 9 mg/g of decoction or 1.8 mg/g of raw botanical. The extraction procedure reflects a depletion of at least 30 fold resulting in an almost undetectable quantity of oxidole alkaloids.

A pharmaceutical dosage comprising a biologically active amount of the Uncaria extract produced as taught herein is contemplated for use singularly or in combination with other ingredients for human and animal use. Moreover particularly, a pharmaceutical dosage comprising a biologically active amount of the Uncaria extract can be embodied in suppositories, oral, topical, injectable or inhalable formats.

The pharmaceutical dosage comprising a biologically active amount of the Uncaria extract is administered in a quantity sufficient to ameliorate conditions characterized by NF-κB activation, oxidant burden, enhanced cytokine production and cell death. The conditions are contemplated to include, but are not limited to, arthritis (both osteoarthritis and rheumatoid), inflammatory bowel disease (IBD), gastritis, chronic inflammation of the eyes, skin, liver, muscles and kidney, fibromyalgia, atherosclerosis, and Alzheimer's disease.

While the invention has been described with reference to specific preferred embodiments and uses, it is certainly not limited to those precise embodiments or uses. Rather, many modifications, variations and applications will become apparent to persons skilled in the art without departure from the scope and spirit of the invention, as defined in the appended claims.

What is claimed is:

1. An extract from genus Uncaria plant material comprising polar constituents and having an oxindole alkaloid content depleted to less than about 0.3 milligrams per gram.

2. The extract in claim 1 wherein the genus Uncaria plant material has a starting oxindole alkaloids content of at least about 9 mg per gram of genus Uncaria plant material.

3. The extract in claim 1 embodied in an internally administered or topically administered pharmaceutical dosage.

4. The pharmaceutical dosage in claim 3 comprising a biologically active amount of said extract sufficient to ameliorate a condition selected from the group consisting of; NF-κB activation, oxidant burden, enhanced cytokine production and cell death.

5. The pharmaceutical dosage in claim 3 comprising a biologically active amount of said extract to ameliorate a conditions selected from the group consisting of; arthritis, inflammatory bowel disease, gastritis, inflammation of the eyes, skin, liver, muscles and kidney, fibromyalgia, atherosclerosis, and Alzheimer's disease.

6. A method of extracting the lipidic components from plants of the genus Uncaria, comprising:

decocting plant material from the genus Uncaria to resolve a decocted extract;

filtering the solid mater from the decocted extract;

combining the filtered decocted extract with an organic solvent;

agitating the combination;

separating the combination into distinct phases to resolve a genus Uncaria extract comprising polar constituents and substantially deplete of lipidic constituents; and evaporating the organic solvent to resolve the polar constituents.

7. The method in claim 6 further comprising, drying the filtered decocted extract prior to the step of combining the decoction with an organic solvent.

8. The method of claim 6 wherein, the Uncaria genus is selected from the group consisting of genera; *Uncaria guianensis, Uncaria homomalla, Uncaria perrottetii, Uncaria pteropoda, Uncaria rhynchopylla* and *Uncaria tomentosa*.

9. The method of claim 6 wherein, the stop of filtering is achieved by a method selected from the group consisting of gravitational filtering and vacuum filtering methods.

10. The method of claim 7 wherein, the step of drying is achieved by a method selected from the group consisting of, air-drying, spray drying, freeze-drying and vacuum drying.

11. The method of claim 6, wherein, the organic solvent is selected from the group consisting of; chloroform and methanol, and ethyl acetate.

12. The method of claim 6 wherein, the step of separating the combination comprises settling the combination.

13. A method of reducing the alkaloid content in an extract from plants of the genus Uncaria, comprising:

decocting the plant material from the genus Uncaria to resolve a decocted extract;

filtering the solid mater from the decocted extract;

combining the filtered decocted extract with an organic solvent;

agitating the combination;

separating the combination to resolve a genus Uncaria extract substantially comprised of polar constituents and substantially devoid of alkaloids; and evaporating the organic solvent to resolve the polar constituents.

14. The method of claim 13 wherein, the step of separating the combination comprises settling the combination.

* * * * *

(12) EX PARTE REEXAMINATION CERTIFICATE (7829th)
United States Patent
Bobrowski

(10) Number: US 6,797,286 C1
(45) Certificate Issued: Oct. 26, 2010

(54) METHODS AND PREPARATIONS OF EXTRACTS OF UNCARIA SPECIES WITH REDUCED ALKALOID CONTENT

(75) Inventor: Paul J. Bobrowski, Scottsdale, AZ (US)

(73) Assignee: Rainforest Nutritionals, Inc., Phoenix, AZ (US)

Reexamination Request:
No. 90/007,468, Mar. 17, 2005

Reexamination Certificate for:
Patent No.: 6,797,286
Issued: Sep. 28, 2004
Appl. No.: 10/674,986
Filed: Sep. 30, 2003

Related U.S. Application Data

(60) Provisional application No. 60/416,730, filed on Oct. 5, 2002.

(51) Int. Cl.
*C11B 1/00* (2006.01)
*C11B 1/10* (2006.01)

(52) U.S. Cl. .......................................... 424/725
(58) Field of Classification Search .................. None
See application file for complete search history.

(56) References Cited

U.S. PATENT DOCUMENTS 5,302,611 A * 4/1994 Keplinger et al. ........... 514/411

6,039,949 A * 3/2000 Pero ........................... 424/769
2002/0197692 A1 * 12/2002 Castillo et al. ............... 435/184

OTHER PUBLICATIONS

Piscoya et al. Inflammation Research. 50: 442–448, Sep. 2001.*
Sandoval et al. Phytomedicine 9: 325–337, May 2002.*
Laus et al. Journal of Chromatography A 662 (1994), pp. 243–249.*
Sheng et al. Phytomedicine. 2000, 7(2): 137–143).*
Sheng, Y., Pero, R.W., Wagner, H., Treatment of chemotheraphy–induced leukopenia in a rat model with aqueous extract from Uncaria tomentosa, Phytomedicine 2000, 137–143, V.7(2).

* cited by examiner

*Primary Examiner* — Evelyn Huang

(57) ABSTRACT

The method herein describes a process for the preparation and extraction of components from plants of the family Rubiaceae indigenous to South America, also known as Cat's Claw or Uña de gato. Cat's claw is an ethnomedicine that contains a variety of constituents, some of which have opposing actions. Oxindole and pentacyclic alkaloids have been proposed to be constituents that stimulate immune function, whereas polar constituents act to suppress immune response. An extract that was devoid of the aforementioned alkaloids would avoid opposing actions that may negate effectiveness or limit therapeutic outcome.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–14 are cancelled.

New claims 15-18 are added and determined to be patentable.

*15. A method of producing a composition having anti-inflammatory and non-immuno stimulation properties, comprising:*

*decocting plant material from genus Uncaria, species tomentosa, to resolve a decocted extract;*

*filtering the solid mater from the decocted extract;*

*combining the filtered decocted extract with an organic solvent;*

*agitating the combination;*

*separating the combination into distinct phases to resolve a genus Uncaria, species tomentosa, derived composition comprising polar constituents and less than 0.3 mg/g of oxindole alkaloids; and*

*evaporating the organic solvent to resolve the polar components.*

*16. The method in claim 15 wherein,*

*the plant material has a starting oxindole alkaloid content of at least about 9 mg per gram.*

*17. The method in claim 15 wherein,*

*the composition has thirty times less oxindole alkaloid content than the parent botanical.*

*18. The method in claim 15 wherein,*

*the genus Uncaria, species tomentosa, derived composition inhibits inflammation by inhibiting the formation tumor necrosis factor alpha (TNFα).*

\* \* \* \* \*